US011866060B1

United States Patent
Lyle

(10) Patent No.: US 11,866,060 B1
(45) Date of Patent: *Jan. 9, 2024

(54) ROUTING OR DRIVING SYSTEMS AND METHODS BASED ON SLEEP PATTERN INFORMATION

(71) Applicant: United Services Automobile Association (USAA), San Antonio, TX (US)

(72) Inventor: Ruthie D. Lyle, Durham, NC (US)

(73) Assignee: United Services Automobile Association (USAA), San Antonio, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/453,399

(22) Filed: Nov. 3, 2021

Related U.S. Application Data

(63) Continuation of application No. 16/520,606, filed on Jul. 24, 2019, now Pat. No. 11,180,158.
(Continued)

(51) Int. Cl.
*A01K 1/00* (2006.01)
*B60W 50/14* (2020.01)
(Continued)

(52) U.S. Cl.
CPC .............. *B60W 50/14* (2013.01); *A61B 5/18* (2013.01); *A61B 5/4809* (2013.01);
(Continued)

(58) Field of Classification Search
CPC .. B60W 50/14; B60W 40/09; B60W 2556/00; B60W 2040/0827;
(Continued)

(56) References Cited

U.S. PATENT DOCUMENTS

| | | | | |
|---|---|---|---|---|
| 5,743,349 A | * | 4/1998 | Steinberg | B60K 28/063 180/272 |
| 6,552,649 B1 | * | 4/2003 | Okada | G07C 9/00309 340/10.33 |

(Continued)

OTHER PUBLICATIONS

Daza et al., Fusion of Optimized Indicators from Advanced Driver Assistance (ADAS) for Driver Drowsiness Detection (Year: 2014).
(Continued)

*Primary Examiner* — Quang Pham
(74) *Attorney, Agent, or Firm* — Fletcher Yoder, P.C.

(57) ABSTRACT

A system that detects and reduces impaired driving includes a first sensor that detects information indicative of a sleep pattern of a user, and a second sensor that detect vehicle operation information. The system also include a mobile electronic device communicatively coupled to the first sensor and the second sensor. The mobile electronic device includes a processor and a memory. The memory stores instructions that, when executed by the processor, cause the processor to determine that the user is impaired based on the information indicative of the sleep pattern of the user, and determine that a vehicle is in operation based on the vehicle operation information. The instructions also cause the processor to perform an action to reduce impaired driving in response to determining that the user is impaired and that the vehicle is in operation.

17 Claims, 3 Drawing Sheets

Related U.S. Application Data

(60) Provisional application No. 62/712,655, filed on Jul. 31, 2018.

(51) Int. Cl.

| | |
|---|---|
| *B60W 40/09* | (2012.01) |
| *A61B 5/18* | (2006.01) |
| *B60Q 9/00* | (2006.01) |
| *A61B 5/00* | (2006.01) |
| *G01C 21/34* | (2006.01) |
| *G08B 21/06* | (2006.01) |
| *B60W 40/08* | (2012.01) |

(52) U.S. Cl.
CPC .......... *A61B 5/6892* (2013.01); *A61B 5/6898* (2013.01); *B60Q 9/00* (2013.01); *B60W 40/09* (2013.01); *G01C 21/3415* (2013.01); *G08B 21/06* (2013.01); *B60W 2040/0827* (2013.01); *B60W 2050/143* (2013.01); *B60W 2050/146* (2013.01); *B60W 2540/26* (2013.01); *B60W 2556/00* (2020.02)

(58) Field of Classification Search
CPC ..... B60W 2050/143; B60W 2050/146; B60W 2540/26; A61B 5/18; A61B 5/4809; A61B 5/6892; A61B 5/6898; B60Q 9/00; G01C 21/3415; G08B 21/06
See application file for complete search history.

(56) References Cited

U.S. PATENT DOCUMENTS

| | | | | |
|---|---|---|---|---|
| 6,697,732 B1* | 2/2004 | Gotfried | ............... | B60K 28/063 |
| | | | | 701/1 |
| 8,213,962 B2* | 7/2012 | Carr | ................... | H04B 5/0031 |
| | | | | 455/26.1 |
| 8,340,902 B1* | 12/2012 | Chiang | ................ | G05D 1/0044 |
| | | | | 382/104 |
| 8,942,779 B2* | 1/2015 | Halperin | .................. | A61B 5/08 |
| | | | | 600/347 |
| 9,549,702 B1* | 1/2017 | Kerness | ............... | A61B 5/4845 |
| 9,707,845 B1* | 7/2017 | Nienhouse | ........... | B60K 28/063 |
| 9,809,228 B2* | 11/2017 | Hong | ................. | B60K 28/066 |
| 9,870,689 B1* | 1/2018 | Deluca | ................... | G04G 13/02 |
| 9,966,059 B1* | 5/2018 | Ayrapetian | ............... | H04R 1/08 |
| 9,988,055 B1* | 6/2018 | O'Flaherty | ........... | G08B 21/06 |
| 10,092,219 B2* | 10/2018 | Arnold | ............... | A61B 5/02055 |
| 10,214,118 B1* | 2/2019 | Jain | ......................... | B60K 35/00 |
| 10,227,003 B1* | 3/2019 | Sanchez | ................. | G08B 21/06 |
| 10,235,859 B1* | 3/2019 | Hiles | ......................... | A61B 5/18 |
| 10,325,514 B2* | 6/2019 | Arnold | ................. | A61B 5/4815 |
| 10,384,602 B1* | 8/2019 | Csabi | ....................... | B60Q 9/008 |
| 10,401,807 B2* | 9/2019 | Jo | ............................ | G08C 17/02 |
| 10,654,414 B1* | 5/2020 | Csabi | ....................... | B60Q 9/008 |
| 11,021,164 B2* | 6/2021 | Tibbitts | ................ | B60W 40/09 |
| 11,180,158 B1* | 11/2021 | Lyle | ....................... | B60W 40/09 |
| 11,198,389 B1* | 12/2021 | Csabi | ....................... | B60Q 9/008 |
| 2005/0177051 A1* | 8/2005 | Almen | ............... | A61B 5/02438 |
| | | | | 600/509 |
| 2006/0200008 A1* | 9/2006 | Moore-Ede | ........... | B60K 28/06 |
| | | | | 128/920 |
| 2007/0024454 A1* | 2/2007 | Singhal | .................. | G08B 21/06 |
| | | | | 340/576 |
| 2008/0231703 A1* | 9/2008 | Nagata | ................... | H04N 7/181 |
| | | | | 348/E7.086 |
| 2009/0147996 A1* | 6/2009 | Peng | ....................... | G01S 11/12 |
| | | | | 382/106 |
| 2009/0160631 A1* | 6/2009 | Galley | ................. | B60K 28/066 |
| | | | | 340/439 |
| 2011/0304465 A1* | 12/2011 | Boult | ..................... | B60K 28/06 |
| | | | | 340/576 |
| 2012/0078473 A1* | 3/2012 | Ridder | .................. | A61B 5/1455 |
| | | | | 701/45 |
| 2012/0112879 A1* | 5/2012 | Ekchian | ............. | A61B 5/14546 |
| | | | | 340/5.53 |
| 2012/0212353 A1* | 8/2012 | Fung | ....................... | G08G 1/167 |
| | | | | 701/1 |
| 2012/0253154 A1* | 10/2012 | Phillips | .................. | A61B 5/117 |
| | | | | 600/509 |
| 2012/0286957 A1* | 11/2012 | Frechette | ............. | B60K 28/066 |
| | | | | 340/575 |
| 2012/0303199 A1* | 11/2012 | Oba | ..................... | B60L 15/2009 |
| | | | | 903/902 |
| 2013/0009761 A1* | 1/2013 | Horseman | ............ | A61B 5/6893 |
| | | | | 340/576 |
| 2013/0093603 A1* | 4/2013 | Tschirhart | ................ | A61B 5/18 |
| | | | | 340/902 |
| 2013/0167207 A1* | 6/2013 | Davis | ..................... | G06F 21/316 |
| | | | | 726/5 |
| 2013/0181500 A1* | 7/2013 | Buehlmeyer | ............ | B60N 2/24 |
| | | | | 297/463.1 |
| 2013/0217990 A1* | 8/2013 | Saettel | .................... | B60K 28/06 |
| | | | | 600/365 |
| 2013/0238226 A1* | 9/2013 | Slaymaker | ............ | F02D 41/062 |
| | | | | 701/113 |
| 2014/0048551 A1* | 2/2014 | Slipe, Sr. | ........... | B65D 81/3879 |
| | | | | 220/739 |
| 2014/0059066 A1* | 2/2014 | Koloskov | ............... | G06F 16/40 |
| | | | | 361/679.01 |
| 2014/0111647 A1* | 4/2014 | Atsmon | .................... | G08G 1/14 |
| | | | | 348/148 |
| 2014/0128760 A1* | 5/2014 | Saunders | ............... | A61B 5/082 |
| | | | | 600/532 |
| 2014/0179348 A1* | 6/2014 | Simon | .................... | H04W 4/029 |
| | | | | 455/456.1 |
| 2014/0231166 A1* | 8/2014 | Miller | ..................... | B60K 28/06 |
| | | | | 180/272 |
| 2014/0256303 A1* | 9/2014 | Jones | ..................... | H04W 4/029 |
| | | | | 455/418 |
| 2014/0266789 A1* | 9/2014 | Matus | ...................... | H04Q 9/00 |
| | | | | 340/870.07 |
| 2014/0334645 A1* | 11/2014 | Yun | ........................ | G10L 15/22 |
| | | | | 381/110 |
| 2014/0335814 A1* | 11/2014 | Gudlavenkatasiva | ...................... | |
| | | | | H04W 76/50 |
| | | | | 455/404.1 |
| 2014/0343831 A1* | 11/2014 | Hosey | ................... | H02J 7/0032 |
| | | | | 324/426 |
| 2014/0347366 A1* | 11/2014 | Emori | ..................... | A61B 5/742 |
| | | | | 345/440 |
| 2014/0364770 A1* | 12/2014 | Slonneger | ............... | G01P 21/00 |
| | | | | 600/595 |
| 2014/0375462 A1* | 12/2014 | Biondo | .................. | A61B 5/18 |
| | | | | 340/576 |
| 2015/0019266 A1* | 1/2015 | Stempora | ............... | G06Q 40/08 |
| | | | | 705/4 |
| 2015/0022338 A1* | 1/2015 | Hwang | .................. | G08B 5/222 |
| | | | | 340/501 |
| 2015/0025917 A1* | 1/2015 | Stempora | ............ | G02B 27/0093 |
| | | | | 705/4 |
| 2015/0026647 A1* | 1/2015 | Park | ...................... | G06F 1/3231 |
| | | | | 715/863 |
| 2015/0029014 A1* | 1/2015 | Bande | .................... | G08B 21/06 |
| | | | | 340/439 |
| 2015/0065082 A1* | 3/2015 | Sehgal | .................. | G08B 25/016 |
| | | | | 455/404.2 |
| 2015/0066284 A1* | 3/2015 | Yopp | ...................... | H04W 76/50 |
| | | | | 701/29.2 |
| 2015/0127570 A1* | 5/2015 | Doughty | ............... | G06Q 50/265 |
| | | | | 705/325 |
| 2015/0149042 A1* | 5/2015 | Cooper | ................ | B60R 25/245 |
| | | | | 701/48 |
| 2015/0204965 A1* | 7/2015 | Magarida | .......... | H04M 1/72454 |
| | | | | 367/117 |
| 2015/0254955 A1* | 9/2015 | Fields | ................. | G06Q 30/0283 |
| | | | | 340/576 |
| 2015/0324698 A1* | 11/2015 | Karaoguz | ............... | H04L 67/12 |
| | | | | 706/46 |

(56) References Cited

U.S. PATENT DOCUMENTS

| | | | |
|---|---|---|---|
| 2015/0328985 A1* | 11/2015 | Kim | G08B 21/06 180/272 |
| 2015/0329121 A1* | 11/2015 | Lim | H04M 1/72412 701/36 |
| 2015/0351681 A1* | 12/2015 | Lee | G08B 21/06 600/595 |
| 2015/0355612 A1* | 12/2015 | Franceschetti | A61B 5/0816 700/275 |
| 2015/0360564 A1* | 12/2015 | Kalbus | H04W 4/48 701/36 |
| 2016/0001781 A1* | 1/2016 | Fung | G07C 9/37 701/36 |
| 2016/0007934 A1* | 1/2016 | Arnold | A61B 5/1118 600/595 |
| 2016/0029940 A1* | 2/2016 | Iizuka | B60K 28/00 701/23 |
| 2016/0044575 A1* | 2/2016 | Rajeevalochana | H04W 8/245 455/410 |
| 2016/0051184 A1* | 2/2016 | Wisbey | A61B 5/6817 600/595 |
| 2016/0052391 A1* | 2/2016 | Walsh | G08B 21/06 340/575 |
| 2016/0066716 A1* | 3/2016 | Rao | A61B 5/6814 600/26 |
| 2016/0071393 A1* | 3/2016 | Kaplan | A61B 5/162 340/539.12 |
| 2016/0151603 A1* | 6/2016 | Shouldice | A61M 21/02 600/26 |
| 2016/0165031 A1* | 6/2016 | Gopinath | H04W 8/005 455/569.2 |
| 2016/0180677 A1* | 6/2016 | Reed | H04W 4/70 340/576 |
| 2016/0192879 A1* | 7/2016 | Yamashita | A61B 5/721 600/407 |
| 2016/0235359 A1* | 8/2016 | Cho | A61B 5/4809 |
| 2016/0267335 A1* | 9/2016 | Hampiholi | B60K 28/066 |
| 2016/0297431 A1* | 10/2016 | Eigel | B60W 30/06 |
| 2016/0303967 A1* | 10/2016 | Quix | B60W 50/0098 |
| 2016/0318395 A1* | 11/2016 | Cofer | G08B 25/08 |
| 2016/0327407 A1* | 11/2016 | Park | G01P 15/00 |
| 2017/0003666 A1* | 1/2017 | Nunn | G16H 40/63 |
| 2017/0035212 A1* | 2/2017 | Erko | A47C 27/083 |
| 2017/0035332 A1* | 2/2017 | Wahnschafft | A45C 11/00 |
| 2017/0054842 A1* | 2/2017 | Choi | H04M 1/72463 |
| 2017/0086732 A1* | 3/2017 | Tribble | A61B 5/746 |
| 2017/0101111 A1* | 4/2017 | Fung | B60K 35/00 |
| 2017/0105104 A1* | 4/2017 | Ulmansky | H04W 4/42 |
| 2017/0106858 A1* | 4/2017 | Li | B60W 30/09 |
| 2017/0112391 A1* | 4/2017 | Stivoric | A61B 5/0022 |
| 2017/0136203 A1* | 5/2017 | Swain | A61M 16/109 |
| 2017/0154533 A1* | 6/2017 | Illy | G08G 1/167 |
| 2017/0166054 A1* | 6/2017 | Ayala Rodriguez | A61B 5/18 |
| 2017/0193982 A1* | 7/2017 | Agrawal | G06V 40/20 |
| 2017/0210288 A1* | 7/2017 | Briggs | B60C 9/00 |
| 2017/0282792 A1* | 10/2017 | Illy | B60W 40/08 |
| 2017/0287501 A1* | 10/2017 | Matsumoto | G10L 21/028 |
| 2017/0300655 A1* | 10/2017 | Lane | G16H 10/60 |
| 2017/0312477 A1* | 11/2017 | Hashizaki | A61B 5/4815 |
| 2017/0316685 A1 | 11/2017 | Yun | |
| 2017/0319063 A1* | 11/2017 | Verdooner | A61B 5/4809 |
| 2017/0355377 A1* | 12/2017 | Vijaya Kumar | B60W 50/0098 |
| 2017/0365165 A1* | 12/2017 | Landfors | B60W 40/09 |
| 2018/0004211 A1* | 1/2018 | Grimm | G06Q 50/28 |
| 2018/0012085 A1* | 1/2018 | Blayvas | G06F 18/2414 |
| 2018/0033307 A1* | 2/2018 | Tayama | G08G 1/16 |
| 2018/0037228 A1* | 2/2018 | Biondo | B60K 28/063 |
| 2018/0063319 A1* | 3/2018 | Kadous | H04M 1/72463 |
| 2018/0072310 A1* | 3/2018 | Fung | B60W 50/14 |
| 2018/0093672 A1* | 4/2018 | Terwilliger | G08B 21/06 |
| 2018/0105180 A1* | 4/2018 | Fung | A61B 5/1122 |
| 2018/0116415 A1* | 5/2018 | Karschnik | A47C 31/008 |
| 2018/0116604 A1* | 5/2018 | Newberry | A61B 5/4845 |
| 2018/0126901 A1* | 5/2018 | Levkova | B60W 40/09 |
| 2018/0143635 A1* | 5/2018 | Zijderveld | G05D 1/0291 |
| 2018/0144714 A1* | 5/2018 | Khorasani | G09G 5/02 |
| 2018/0146354 A1* | 5/2018 | Patel | H04W 4/90 |
| 2018/0154903 A1* | 6/2018 | Song | G06V 40/107 |
| 2018/0173230 A1* | 6/2018 | Goldman-Shenhar | B60W 50/14 |
| 2018/0174457 A1 | 6/2018 | Taylor | |
| 2018/0178808 A1* | 6/2018 | Zhao | B60K 28/066 |
| 2018/0186234 A1* | 7/2018 | Mestha | A61B 5/18 |
| 2018/0244288 A1* | 8/2018 | Glaser | B60W 50/14 |
| 2018/0281807 A1* | 10/2018 | Minegishi | G06V 20/597 |
| 2018/0281808 A1* | 10/2018 | Minegishi | B60W 50/14 |
| 2018/0301919 A1* | 10/2018 | Rumbaugh | H01M 50/244 |
| 2018/0312164 A1* | 11/2018 | Sasabuchi | B60W 30/18018 |
| 2018/0322266 A1* | 11/2018 | Kwok-Suzuki | H04L 63/0861 |
| 2018/0348759 A1* | 12/2018 | Freeman | A61N 1/3904 |
| 2018/0365998 A1* | 12/2018 | Shibata | G08G 1/096791 |
| 2018/0368757 A1* | 12/2018 | Amin | G16H 40/67 |
| 2019/0008450 A1* | 1/2019 | Gurievsky | A61B 5/4812 |
| 2019/0010719 A1* | 1/2019 | Secrest | E04G 23/0288 |
| 2019/0011914 A1* | 1/2019 | Park | B60W 40/08 |
| 2019/0038204 A1* | 2/2019 | Beck | A61B 5/024 |
| 2019/0046120 A1* | 2/2019 | Sham | A61B 5/11 |
| 2019/0052748 A1* | 2/2019 | Stewart | H04M 1/72463 |
| 2019/0056732 A1* | 2/2019 | Aoi | B60W 40/08 |
| 2019/0064805 A1* | 2/2019 | Frazzoli | G05D 1/0246 |
| 2019/0070386 A1* | 3/2019 | Raut | A61B 5/4812 |
| 2019/0082044 A1* | 3/2019 | Melendez | H04W 4/023 |
| 2019/0092337 A1* | 3/2019 | Chua | B60W 30/14 |
| 2019/0100216 A1* | 4/2019 | Volos | G06Q 40/08 |
| 2019/0122525 A1* | 4/2019 | Lancelle | B60Q 9/00 |
| 2019/0178218 A1* | 6/2019 | Anderson | F02N 11/101 |
| 2019/0180283 A1* | 6/2019 | Unnerstall | A61B 5/4812 |
| 2019/0187701 A1* | 6/2019 | Zheng | B60W 50/14 |
| 2019/0202464 A1* | 7/2019 | McGill | B60W 60/0053 |
| 2019/0223773 A1* | 7/2019 | Galm | G16H 50/20 |
| 2019/0279447 A1* | 9/2019 | Ricci | A61B 5/4809 |
| 2019/0293171 A1* | 9/2019 | Cuddihy | F16H 63/48 |
| 2019/0299895 A1* | 10/2019 | Herbert | B60R 21/01554 |
| 2019/0299897 A1* | 10/2019 | Gramenos | B60N 2/4279 |
| 2019/0303729 A1* | 10/2019 | Gramenos | G06V 20/593 |
| 2019/0315369 A1* | 10/2019 | Thompson | B60W 60/00 |
| 2019/0357834 A1* | 11/2019 | Aarts | A61B 5/7246 |
| 2020/0015058 A1* | 1/2020 | Wu | H04W 76/50 |
| 2020/0020165 A1* | 1/2020 | Tran | G06F 3/011 |
| 2020/0094737 A1* | 3/2020 | Furukawa | B60W 30/0956 |
| 2020/0122731 A1* | 4/2020 | Vanhelle | B60K 28/06 |
| 2020/0198465 A1* | 6/2020 | Tanabe | G08G 1/00 |
| 2020/0290626 A1* | 9/2020 | Chen | B60K 35/00 |
| 2020/0393835 A1* | 12/2020 | Gregg | G01C 21/3438 |
| 2021/0081688 A1* | 3/2021 | Bazargan | G06V 40/10 |
| 2021/0291838 A1* | 9/2021 | Tamilarasan | G06V 40/18 |
| 2021/0307621 A1* | 10/2021 | Svenson | A61B 5/024 |
| 2022/0032920 A1* | 2/2022 | Varughese | H04W 4/40 |

OTHER PUBLICATIONS

Dong et al., Driver Inattention Monitoring System for Intelligent Vehicles (Year: 2011).

Sena et al., A Fuzzy Model to Interpret Data of Drive Performances from Patients with Sleep Deprivation (Year: 2012).

Vascones et al., Sleepiness Detection for Cooperative Vehicle Navigation Strategies (Year: 2018).

Yang et al., Detection of Driver Fatigue Caused by Sleep Deprivation (Year: 2009).

* cited by examiner

ROUTING OR DRIVING SYSTEMS AND METHODS BASED ON SLEEP PATTERN INFORMATION

CROSS-REFERENCE TO RELATED APPLICATION

This application is a continuation of U.S. Non-Provisional application Ser. No. 16/520,606 filed Jul. 24, 2019, which claims the benefit of U.S. Provisional Application No. 62/712,655 filed Jul. 31, 2018, which is herein incorporated by reference in its entirety for all purposes.

BACKGROUND OF THE INVENTION

The present disclosure relates generally to driving systems, and more particularly to systems and methods for using sleep pattern information to detect and reduce impaired driving.

This section is intended to introduce the reader to various aspects of art that may be related to various aspects of the present disclosure, which are described and/or claimed below. This discussion is believed to help provide the reader with background information to facilitate a better understanding of the various aspects of the present disclosure. Accordingly, it is understood that these statements are to be read in this light, and not as admissions of prior art.

A variety of factors may cause impaired driving, such as drowsiness due to lack of sleep, medication, other drugs (e.g., alcohol), and the like. It is now recognized that systems and methods for detecting such factors and mitigating effects on driving are desirable.

BRIEF DESCRIPTION OF THE DRAWINGS

Various aspects of this disclosure may be better understood upon reading the following detailed description and upon reference to the drawings in which.

DETAILED DESCRIPTION OF SPECIFIC EMBODIMENTS

Figure 1:
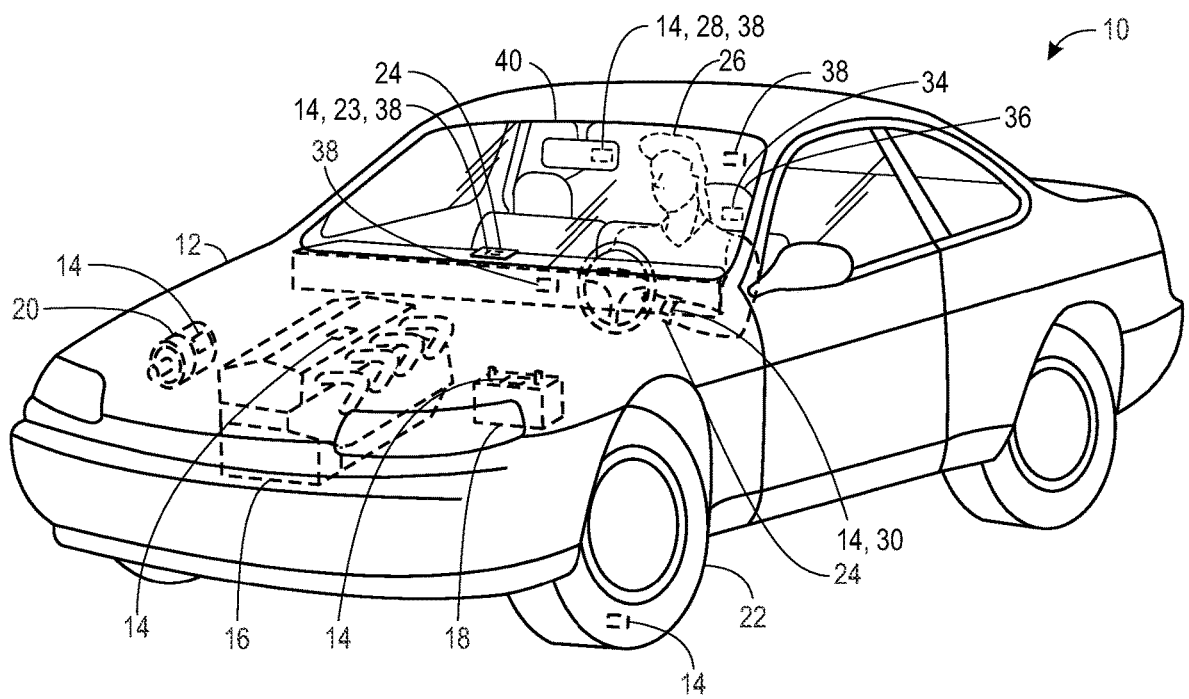
FIG. 1 is a perspective view of an impaired driving detection and reduction system used in a vehicle, according to an embodiment of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is now recognized that certain detectable characteristics may be associated with impaired (e.g., distracted) driving, such as correlating a manner in which a driver is operating a vehicle with sleep pattern information. Further, it is now recognized that instances of impaired driving may be reduced by determining whether the driver is impaired, based on the detectable characteristics, and performing actions to alert the driver, offering alternatives to operating the vehicle while impaired, incentivizing the driver to not operate the vehicle while impaired, penalizing the driver for operating the vehicle, and/or warning nearby drivers or autonomous vehicles.

The present disclosure relates generally to impaired driving, and more particularly to systems and methods for using sleep pattern information to detect and reduce impaired driving. In some embodiments, a sleep pattern sensor of a sleep pattern device (e.g., a mattress overlay sleep tracker, a wearable biometric device, a mobile communication device executing a sleep pattern software application) may detect sleep pattern information (e.g., when a user is typically asleep or when the user is typically awake) of a user. A vehicle sensor (e.g., a speedometer, an accelerometer, a location device, or a global positioning system device) may indicate that the user is operating the vehicle. An electronic device (e.g., mobile electronic device or a vehicle operation tracking device) may then perform an action to alert the driver, offer alternatives to operating the vehicle while impaired, incentivize the driver to not operate the vehicle while impaired (e.g., via offering discounts associated with auto insurance, products, services or gamification), penalize the driver for operating the vehicle (e.g., via increasing payments associated with auto insurance or gamification), contact a person familiar with the user, contact a call center (e.g., associated with the user's insurance company), or warn nearby drivers or autonomous vehicles. In the present context, gamification includes using any suitable gaming elements to encourage the user to not drive while impaired or discourage the user from driving while impaired. For example, such gaming elements may include rewarding the user with points, achievement badges or levels, filling a progress bar, and/or providing the user with virtual currency. Similarly, such gaming elements may also or alternatively include decreasing user points, taking away achievement badges or levels, decreasing a progress bar, and/or taking away virtual currency.

In this manner, the disclosed systems and methods may reduce impaired driving. In additional or alternative embodiments, the electronic device may send an indication to nearby drivers within a threshold distance from the user that the user is determined to be impaired. This may alert the nearby drivers to the impaired driver, reducing traffic incidents.

As an introduction, FIG. 1 is a perspective view of an impaired driving detection and reduction system 10 used in a vehicle 12, according to an embodiment of the present disclosure. While the vehicle 12 is illustrated as an automobile, it should be understood that the present disclosure applies to any suitable vehicle, such as a truck, motorcycle, commercial vehicle, recreational vehicle, all-terrain vehicle, boat, airplane, snowmobile, and the like. The vehicle 12 may include one or more vehicle operation sensors 14 that detect or determine whether the vehicle 12 is in operation. For example, the vehicle operation sensors 14 may include an engine sensor that monitors whether an engine 16 of the vehicle 12 is running. The vehicle operation sensors 14 might include a battery sensor that detects whether a battery 18 of the vehicle 12 is being drained (e.g., to start the vehicle 12). In some embodiments, the vehicle operation sensors 14 may include an alternator sensor that determines whether an alternator 20 of the vehicle 12 is attempting to start the vehicle 12. The vehicle operation sensors 14 may include a wheel sensor that detects whether a wheel 22 of the vehicle 12 is rotating. In further embodiments, other sensors (such as front or rear facing cameras 23) of the vehicle 12 may be used to determine that the vehicle 12 is in operation. Additionally or alternatively, sensors external to the vehicle 12 may be used to determine that the vehicle 12 is in operation. For example, the vehicle operation sensors 14 may include location sensors, orientation sensors, and/or motion sensors of a mobile electronic device 24 that determine that, based on the sensed location, orientation, and/or motion (e.g., calculated velocity and/or acceleration) of the mobile electronic device 24, a user 26 is in the vehicle 12 and the vehicle 12 is in operation. It should be understood that the vehicle operation sensors 14 listed above are merely examples, and that any suitable sensor that indicates that the vehicle 12 is in operation is contemplated as a vehicle operation sensor 14.

The vehicle 12 may also include one or more impairment sensors 28 that facilitate determining whether the user 26 is impaired. For example, an impairment sensor 28 may include a pulse detection sensor 30 in a steering wheel 32 of the vehicle 12 that may measure a pulse of the user 26. As another example, the impairment sensor 28 may include a biometric or occupancy sensor 34 in a driver's seat 36 of the vehicle 12 that may sense biometric information of the user 26, such as the pulse of the user 26. In some cases, the impairment sensor 28 may include an eye or head detection sensor 38 (e.g., a camera) in a windshield 40, in a mirror 42, or mounted on a dashboard 44 of the vehicle 12, that may determine eye focus or head movement or direction of the user 26. In some embodiments, the impairment sensor 28 may not be integrated into the vehicle 12. For example, the impairment sensor 28 may include a pulse detection sensor 30 or other biometric sensor of a mobile electronic device 24 (e.g., a wearable electronic device) or a camera 23 or eye or head detection sensor 38 of a mobile electronic device 24 (e.g., a smartphone). As illustrated, an impairment sensor 28 may also be used as a vehicle operation sensor 14. For example, the rear facing camera 23 may be used both to determine that the vehicle 12 is in operation as a vehicle operation sensor 14 and to facilitate determining whether the user 26 is impaired as an impairment sensor 28.

The mobile electronic device 24 may include any suitable electronic device that may communicate information to the user 26 via, for example, a communication network, such as a smartphone, a wearable electronic device, a computing device, a laptop, a tablet, a vehicle operation tracking device (such as those used by insurance companies), and the like. The mobile electronic device 24 may be used to communicate with the user 26 when it is determined that the user 26 may be impaired, such as by alerting the user 26, offering alternatives to operating the vehicle 12, incentivizing the user 26 to not operate the vehicle 12 (e.g., via offering discounts associated with auto insurance, products, services, or gamification), penalizing the user 26 (e.g., via increasing payments associated with auto insurance or gamification, contacting a person familiar with the user 26, contacting a call center, and/or warning nearby drivers or autonomous vehicles.

Figure 2:
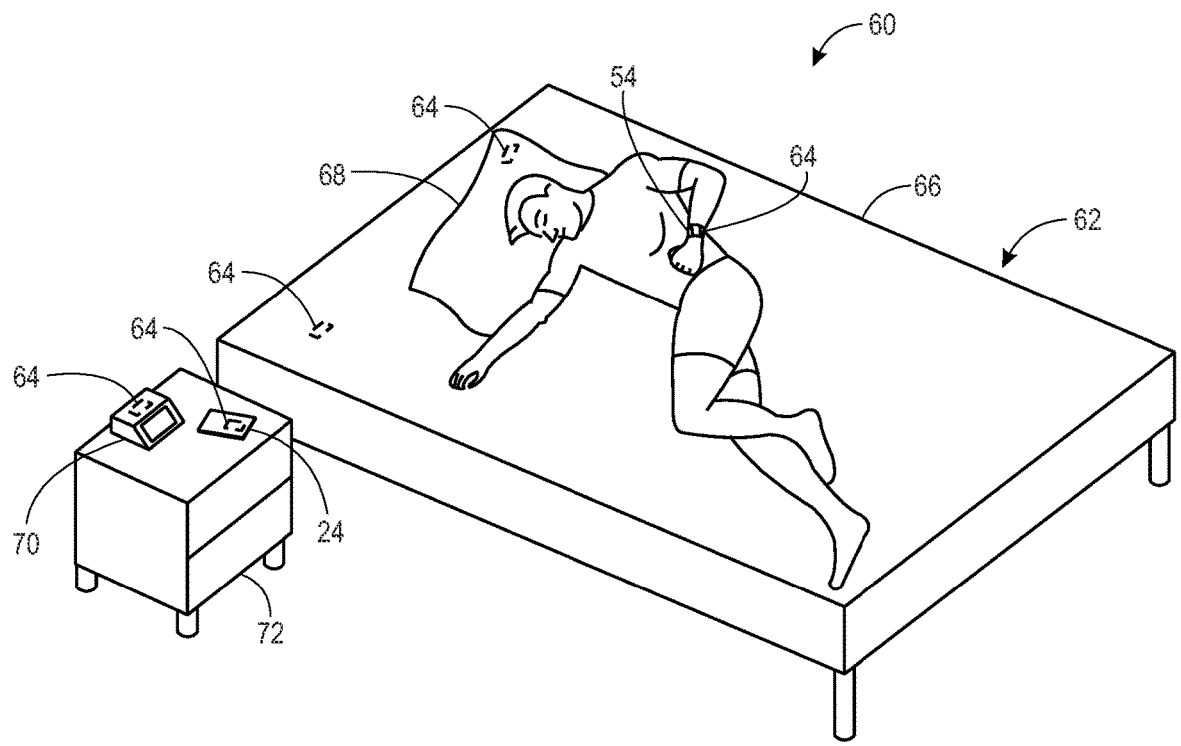
FIG. 2 is a perspective view of a sleep pattern information gathering system, which may gather sleep pattern information to be used by the impaired driving detection and reduction system of FIG. 1, according to an embodiment of the present disclosure.

The impaired driving detection and reduction system 10 may determine that the user 26 is impaired based on sleep pattern information of the user 26. FIG. 2 is a perspective view of a sleep pattern information gathering system 60, which may gather sleep pattern information to be used by the impaired driving detection and reduction system 10 of FIG. 1, according to an embodiment of the present disclosure. As illustrated, the user 26 may be sleeping in a bed 62. Any suitable sleep pattern sensor 64 may be used to detect and/or gather sleep pattern information of the user 26. Sleep pattern information, including timed patterns of sleep, may be any suitable information that indicates that the user 26 is asleep, is about to fall asleep, is preparing for sleep, is in deep sleep, is undergoing rapid eye movement, is having restless sleep (e.g., generally moves during sleep), is having restful sleep (e.g., generally is still during sleep), and/or is waking from sleep. As such, the sleep pattern information may include information such as when the user 26 is near the bed 62, lies in the bed 62, has closed his or her eyes, pulse information related to sleeping, breathing rate information related to sleeping, heartbeat information related to sleeping, oxygen level information related to sleeping, audio information related to breathing and/or snoring, or any other suitable sounds and/or images indicative of sleep patterns.

As illustrated, the sleep pattern sensor 64 may include, for example, a sleep tracker sensor that is embedded in a mattress overlay 66 or a pillow 68 disposed on the bed 62. In some embodiments, the sleep pattern sensor 64 may include a sleep tracker sensor that is part of a sleep tracking device external to the bed 62, such as a sleep tracking device 70 intended to be placed near the user 26 while the user 26 is sleeping (e.g., on a nightstand 72) or a wearable sleep tracking device 54.

In some embodiments, the sleep pattern information may be determined using any suitable non-sleep related data that may infer sleep pattern information, such as location data or time data, by a processor of the mobile electronic device 24 using any suitable technique, such as artificial intelligence, deep learning, and/or machine learning techniques. For example, location data provided by a location sensor of the mobile electronic device 24 or the user's vehicle may indicate that the user 26 is at home and/or that the mobile electronic device 24 is stationary. Time data may indicate that it is a time within a time range (e.g., 9 PM to midnight) that most people sleep. The processor of the mobile electronic device 24 may determine, using artificial intelligence, deep learning, and/or machine learning techniques, that because the location indicates that the mobile electronic device 24 is stationary and the time data indicates that it is a time within a time range that most people sleep, the user 26 may be asleep. Any suitable sensor may be used to provide the non-sleep related data that may provide sleep pattern information, such as an orientation sensors of the mobile electronic device 24 that may determine that the mobile electronic device 24 is at the user's home, a motion sensor of the mobile electronic device 24 that may determine that the mobile electronic device 24 is stationary, and/or a charging sensor of the mobile electronic device 24 that may determine when the mobile electronic device 24 is charging. Additionally, the mobile electronic device 24 may combine this knowledge with additional information, such as the sleep pattern information determined by the sleep pattern sensor 64.

Figure 3:
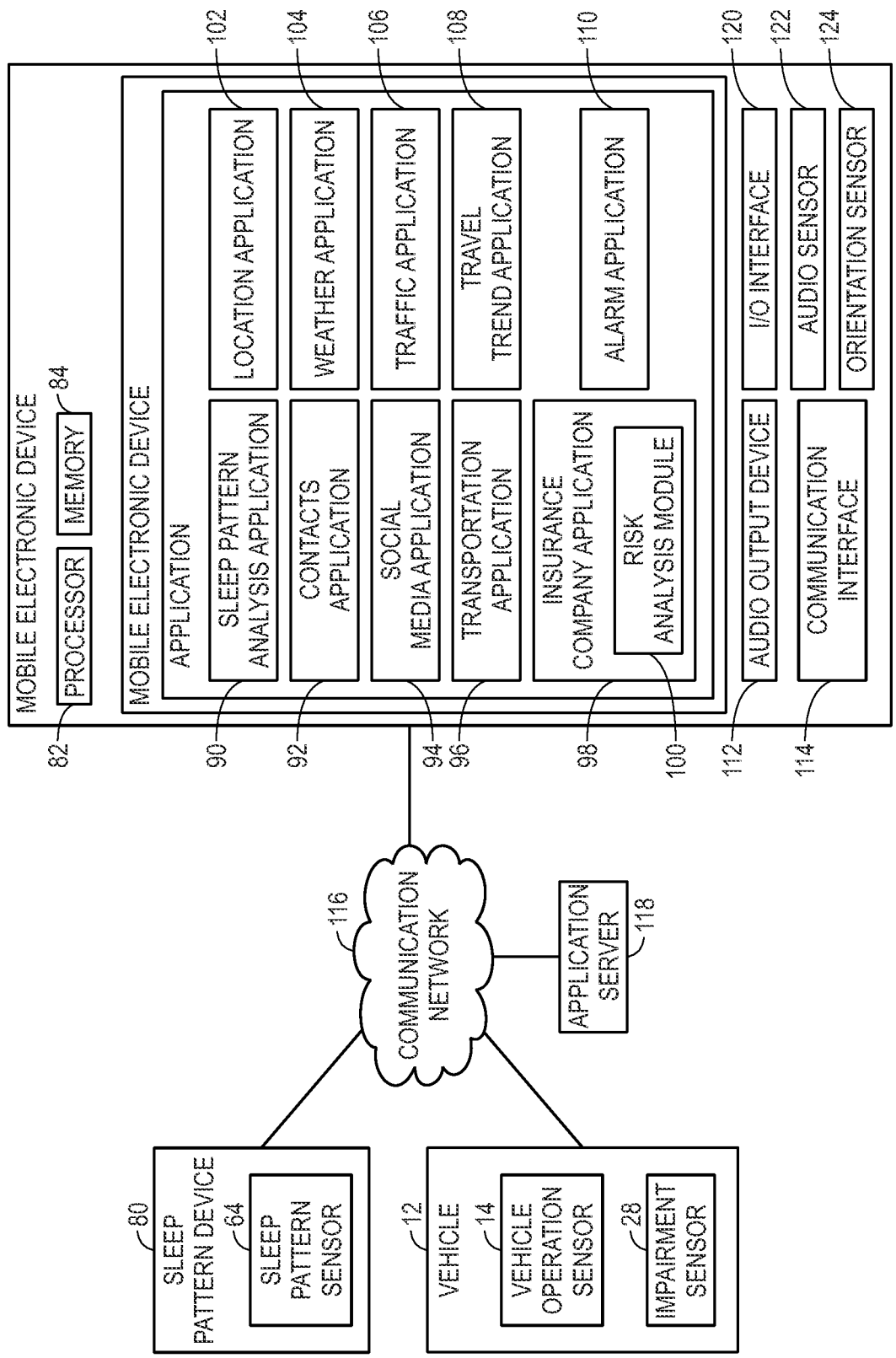
FIG. 3 is a block diagram of the impaired driving detection and reduction system of FIG. 1, according to an embodiment of the present disclosure.

With this in mind, FIG. 3 is a block diagram of the impaired driving detection and reduction system 10 of FIG. 1, according to an embodiment of the present disclosure. The impaired driving detection and reduction system 10 may include a sleep pattern device 80 that includes the sleep pattern sensor 64. That is, the sleep pattern device 80 may include any suitable device that uses the sleep pattern sensor 64 to gather sleep pattern information, such as the mobile electronic device 24, the mattress overlay 66, the pillow 68, the sleep tracking device 70 or the wearable sleep tracking device 54. The impaired driving detection and reduction system 10 may also include the vehicle 12 and the one or more vehicle operation sensors 14 and/or the one or more impairment sensors 28 of the vehicle 12.

The impaired driving detection and reduction system 10 may further include the mobile electronic device 24, which may include one or more processors (illustrated as a single processor 82) and one or more memory devices (illustrated as a single memory device 84). The processor 82 may execute software programs and/or instructions to detect impaired driving characteristics of the user 26 and perform one or more actions to alert the driver, offer alternatives to operating the vehicle while impaired (e.g., requesting alternative transportation, such as via a rideshare software application), incentivize the driver to not operate the vehicle while impaired, penalize the driver for operating the vehicle, or warn nearby drivers or autonomous vehicles. Moreover, the processor 82 may include multiple microprocessors, one or more "general-purpose" microprocessors, one or more special-purpose microprocessors, and/or one or more application specific integrated circuits (ASICS). For example, the processor 82 may include one or more reduced instruction set (RISC) processors. The memory device 84 may store information such as control software, look up tables, configuration data, and so forth. The mobile electronic device 24 may include one or more storage devices (illustrated as a single storage device 86) that may store software applications 88, data, and the like. In some embodiments, the memory device 84 and the storage device 86 may be combined as a single device. The memory device 84 and the storage device 86 may each include a tangible, non-transitory, machine-readable-medium, such as volatile memory (e.g., a random access memory (RAM)), nonvolatile memory (e.g., a read-only memory (ROM)), flash memory, one or more hard drives, and/or any other suitable optical, magnetic, or solid-state storage medium. The memory device 84 and the storage device 86 may each store a variety of information and may be used for various purposes. For example, the storage device 86 may store machine-readable and/or processor-executable instructions (e.g., firmware or software) for the processor 82 to execute, such as instructions for detecting impaired driving characteristics of the user 26, and perform one or more actions to alert the driver, offer alternatives to operating the vehicle while impaired, incentivize the driver to not operate the vehicle while impaired, penalize the driver for operating the vehicle, or warn nearby drivers or autonomous vehicles.

The storage device 86 may store software applications 88 that include instructions which, when executed by the processor 82, perform one or more functions, tasks, and/or activities for the benefit of the user 26. For example, the applications 88 may include a sleep pattern analysis application 90 that receives and analyzes sleep pattern information (e.g., received from the sleep pattern device 80) and determines whether the user 26 is likely to be lacking in or desire sleep, and thus be impaired.

The applications 88 may also include a contacts application 92 that stores contact information of people or services that are of interest to the user 26. In some embodiments, the processor 82 of the mobile electronic device 24 may use the contacts application 92 to communicate (e.g., place a telephone call or sent a text message) to a contact if, for example, the processor 82 determines that the user 26 is impaired. The applications 88 may include one or more social media applications 94 that enable the user 26 to share information with a virtual community or network. In some embodiments, the processor 82 of the mobile electronic device 24 may use the social media application 94 to communicate with a member of a virtual community or network that is familiar to the user 26, for example, the processor 82 determines that the user 26 is impaired. The applications 88 may also include one or more transportation (or rideshare) applications 96 that enable the user 26 to request transportation, such as from a taxi or crowd-sourced transportation company. In some embodiments, the processor 82 of the mobile electronic device 24 may use the transportation application 96 to request transportation from a transportation company if, for example, the processor 82 determines that the user 26 is impaired.

The applications 88 may include an insurance company application 98 that enables the user 26 to communicate with and view or manage accounts the user 26 has with the insurance company. Moreover, the insurance company application 98 may offer the user 26 alternatives to operating the vehicle 12 when the processor 82 determines that the user 26 is impaired. For example, the insurance company application 98 may alert a representative of the insurance company, who may take action to prevent the user 26 from operating the vehicle 12, such as by contacting the user 26. In another example, the insurance company application 98 may incentivize the user 26 to not operate the vehicle 12 while impaired by, for example, offering discounts associated with auto insurance provided by the insurance company or affiliated products or services, or using gaming elements to encourage not driving while impaired. The gaming elements may include any suitable gamification techniques that may encourage the user 26 to not drive while impaired, such as rewarding the user 26 with points, achievement badges or levels, filling a progress bar, and/or providing the user 26 with virtual currency. Similarly, the insurance company application 98 may penalize the user 26 for operating the vehicle 12 while impaired by, for example, increasing payments associated with auto insurance provided by the insurance company or using gaming elements to penalize driving while impaired. Such gaming elements may include any suitable gamification techniques that may discourage the user 26 from driving while impaired, such as decreasing user points, taking away achievement badges or levels, decreasing a progress bar, and/or taking away virtual currency.

The insurance company application 98 may include a risk analysis module 100 that determines a risk factor of the user 26 operating the vehicle 12. The risk analysis module 100 may receive a variety of inputs relating to the user 26, the vehicle 12, travel conditions (e.g., weather, traffic, or historical trends) associated with where the vehicle 12 is located, and output a risk factor (e.g., a numerical representation of the risk of the user 26 operating the vehicle 12 in the travel conditions) based on the variety of inputs. For example, the processor 82 may receive sleep pattern information from the sleep pattern device 80 and determine the risk factor based on the sleep pattern information. That is, if the sleep pattern information indicates that the current time is within a time range that the user 26 typically sleeps, the processor 82 may increase the risk factor. As another example, the processor 82 may receive impairment data from the vehicle 12 (as sensed by the impairment sensor 28) and determine the risk factor based on the impairment data.

If the impairment data indicates that the user 26 may be impaired, then the processor 82 may increase the risk factor.

Moreover, the applications 88 may include a location application 102 that determines a location at which the mobile electronic device 24 is located, a weather application 104 that determines weather conditions at various locations, a traffic application 106 that determines traffic conditions at various locations, and/or a travel trend application 108 that determines travel trend information (e.g., accident history information, crime statistics, or traffic trends at certain times of day, month, or year) at various locations. As such, the processor 82 may determine the risk factor based on weather information received from the weather application 104 for the location received from the location application 102. That is, if the weather information indicates poor driving conditions (e.g., snowing, heavy rain, or ice patches), then the processor 82 may increase the risk factor. Similarly, the processor 82 may determine the risk factor based on traffic information received from the traffic application 106 for the location received from the location application 102. That is, if the traffic information indicates traffic congestion, a nearby accident, or any other traffic condition that may negatively impact operating the vehicle 12, then the processor 82 may increase the risk factor. The processor 82 may also determine the risk factor based on travel trend information received from the travel trend application 106 for the location received from the location application 102. That is, if the travel trend information indicates conditions that should be avoided (e.g., a higher than average chance of traffic incidents, a higher than average rate of crime, nearby construction areas, or poor road conditions), then the processor 82 may increase the risk factor.

The processor 82 may compare the risk factor determined by the risk analysis module 100 to a risk factor threshold, and based on the comparison, may determine whether the user 26 should or should not operate the vehicle 12. In some embodiments, the mobile electronic device 24 may include an alarm application 110 that alerts the user 26 (e.g., via an audio output device 112 of the mobile electronic device 24) when the processor 82 determines that the user 26 should not operate the vehicle 12. In additional or alternative embodiments, the processor 82 may facilitate offering the user 26 alternatives to operating the vehicle 12 via the insurance company application 98. The processor 82 may also warn nearby drivers or autonomous vehicles that the user 26 may be impaired. For example, the processor 82 may receive proximity information from proximity sensor(s) of the vehicle 12 to determine whether there are any nearby vehicles within a threshold distance (e.g., 0-50 feet or 2-25 feet) to the vehicle 12. As another example, the processor 82 may communicate with mobile devices of drivers of the nearby vehicles and/or communication devices of the nearby vehicles or autonomous vehicles to determine whether there are any nearby vehicles within the threshold distance. The processor 82 may then send alerts to the mobile devices of drivers of the nearby vehicles and/or communication devices of the nearby vehicles or autonomous vehicles to inform them that the user 26 may be impaired.

It should be understood that while the functions and/or activities performed by the processor 82 are described as implemented as software applications 88, in some embodiments, these functions and/or activities may be at least partially implemented in hardware (e.g., in the form of logic and/or circuitry of the mobile electronic device 24).

The mobile electronic device 24 may include a communication interface 114 that may enable the processor 82 to communicate with any suitable communication network 116. For example, the communication interface 114 may enable the processor 82 to communicate with wireless networks (e.g., mobile, WiFi, LAN, WAN, or Internet). In this manner, the communication interface 114 may enable the processor 82 to communicate with, for example, an application server 118. The application server 118 may enable the user 26 to communicate with others. For example, the application server 118 may belong to the user's insurance company, and enable the user 26 to communicate with a call center and/or a representative of the insurance company (e.g., via the insurance company application 98). As another example, the application server 118 may belong to a social media network company, and enable the user 26 to communicate with another member of a social media network (e.g., via the social media application 94). As yet another example, the application server 118 may belong to a transportation company, and enable the user 26 to communicate with a user of a transportation network or rideshare service (e.g., via the transportation or rideshare application 96). As illustrated, the communication interface 114 may also enable the processor 82 to communicate with the sleep pattern device 80 and/or the vehicle 12.

The mobile electronic device 24 may also include one or more input/output interfaces 120 that enable the processor 82 to receive and/or transmit signals, such as audio or video signals. For example, the input/output interface 120 may enable the processor 82 to receive audio signals from one or more audio sensors 122 (e.g., microphones) of the mobile electronic device 24. As another example, the input/output interface 120 may enable the processor 82 to transmit audio signals to the one or more audio output devices 112 (e.g., speakers) of the mobile electronic device 24.

The mobile electronic device 24 may also include one or more orientation sensors 124 that enable the processor 82 to determine an orientation of the mobile electronic device 24. For example, an orientation sensor 124 may include a gyroscope that may use the Earth's gravity to determine orientation of the mobile electronic device 24. As another example, the orientation sensor 124 may include an accelerometer that measures proper acceleration, or an acceleration of the mobile electronic device 24 in its own instantaneous rest frame.

Figure 4:
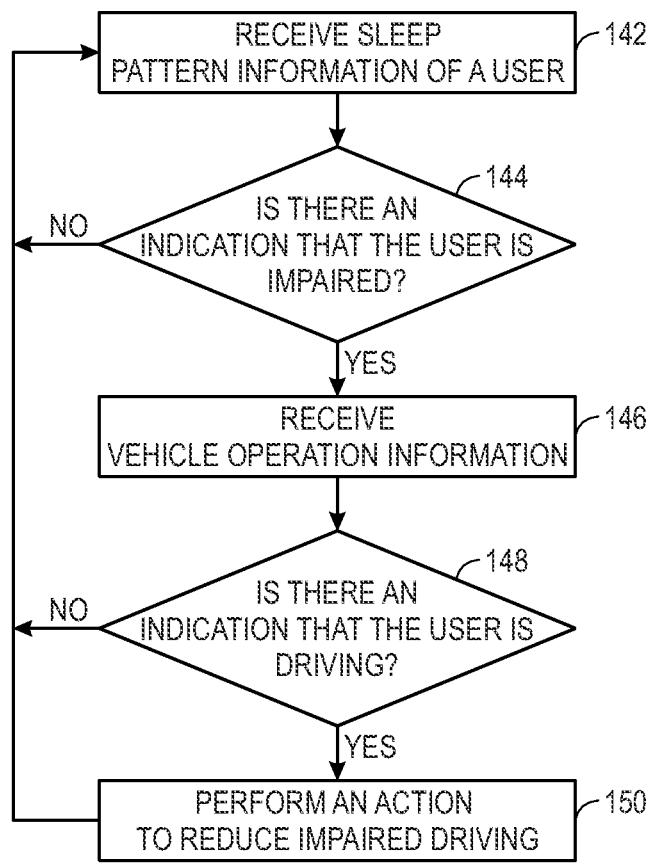
FIG. 4 is a flowchart illustrating a method for detecting and reducing impaired driving, according to an embodiment of the present disclosure.

FIG. 4 is a flowchart illustrating a method 140 for detecting and reducing impaired driving, according to an embodiment of the present disclosure. The method 140 may be performed by any suitable device that may control components of the impaired driving detection and reduction system 10, such as the processor 82. While the method 140 is described using steps in a specific sequence, it should be understood that the present disclosure contemplates that the described steps may be performed in different sequences than the sequence illustrated, and certain described steps may be skipped or not performed altogether. In some embodiments, the method 140 may be implemented by executing instructions stored in a tangible, non-transitory, computer-readable medium, such as the memory device 84, using a processor, such as the processor 82.

As illustrated, the processor 82 receives (block 142) sleep pattern information of the user 26. Specifically, the processor 82 may receive the sleep pattern information from the sleep pattern sensor 64 of the sleep pattern device 80. For example, the sleep pattern information may include a time range that is associated with the user typically being asleep or preparing for sleep. In additional or alternative embodiments, the sleep pattern information may include any suitable information that indicates that the user 26 is asleep, is about to fall asleep, is preparing for sleep, is in deep sleep, evidences rapid eye movement, is having restless sleep (e.g., generally moves during sleep), is having restful sleep (e.g., generally is still during sleep), and/or is waking from sleep from the sleep pattern sensor 64.

The processor 82 then determines (block 144) whether there is an indication that the user 26 is impaired. Specifically, the processor 82 may determine whether there is an indication that the user 26 is impaired based at least in part on the sleep pattern information from block 142. For example, the sleep pattern information may provide a time range that is associated with the user typically being asleep or preparing for sleep, and the processor 82 may determine whether the current time (e.g., the time that the user 26 is attempting to operate or operating the vehicle 12) is within the time range. In some embodiments, the processor 82 may use vehicle operation information to determine whether there is an indication that the user 26 is impaired. For example, the vehicle operation information may include indications of erratic driving behavior, such as swerving of the vehicle 12, abrupt changes in direction of the vehicle 12, lane changes without proper signaling, approaching other vehicles within a threshold distance, abrupt changes in speed of the vehicle 12, and so on. If not, the processor 82 may determine that the user 26 is not impaired, and the method 140 repeats. Otherwise, the processor 82 may determine that the user 26 is impaired. In alternative or additional embodiments, the processor 82 may determine a risk factor based at least in part on the sleep pattern information (e.g., via the risk analysis module 100 of the insurance company application 98). That is, if the sleep pattern information indicates that the current time is within a time range associated with the user 26 typically being asleep or preparing for sleep, the processor 82 may increase the risk factor. The processor 82 may then determine whether the user 26 is impaired based on comparing the risk factor to a risk factor threshold. In particular, the processor 82 may determine that the user 26 is impaired if the risk factor exceeds the risk factor threshold. Otherwise, the processor 82 may determine that the user 26 is not impaired.

Moreover, the processor 82 may determine the risk factor based on impairment data received from one or more impairment sensors of the vehicle 12. For example, the impairment data may include pulse information of the user 26 received from the pulse detection sensor 30. As another example, the impairment data may include biometric information of the user 26 received from the biometric or occupancy sensor 34. In some cases, the impairment data may include eye focus or head movement or direction information of the user 26 received from the eye or head detection sensor 38 (e.g., a camera). In some embodiments, the processor 82 may determine the risk factor based on vehicle operation information. For example, the vehicle operation information may include indications of erratic driving behavior, such as swerving of the vehicle 12, abrupt changes in direction of the vehicle 12, lane changes without proper signaling, approaching other vehicles within a threshold distance, abrupt changes in speed of the vehicle 12, and so on. It should be understood that any suitable technique, including those discussed above, may be used to provide an indication that the user 26 is impaired. Moreover, any combination of techniques may be used to provide an indication that the user 26 is impaired, and any system of accumulating and weighting the results or values resulting from the techniques may be used to provide an indication that the user 26 is impaired.

The processor 82 also receives (block 146) vehicle operation information. Specifically, the vehicle operation information may include sensor data associated with operation of the vehicle 12, and may facilitate determining whether the vehicle 12 is in operation and/or whether the user 26 is operating the vehicle 12. For example, the processor 82 may receive the vehicle operation information from one or more vehicle operation sensors 14. That is, vehicle operation information received from an engine sensor that indicates that the engine 16 of the vehicle 12 is running, a battery sensor that detects that the battery 18 of the vehicle 12 is being drained (e.g., to start the vehicle 12), an alternator sensor that determines that the alternator 20 of the vehicle 12 is attempting to start the vehicle 12, a wheel sensor that detects that the wheel 22 of the vehicle 12 is rotating, or a camera 23 of the vehicle 12 that captures video or image data that indicates that the vehicle 12 is moving, may indicate that the vehicle 12 is in operation. As another example, the processor 82 may receive the vehicle operation information from the orientation sensor 124 and/or a location device, such as a global positioning system device, of the mobile electronic device 24. In additional or alternative embodiments, the vehicle operation information may be provided by the location application 102 of the mobile electronic device 24. In some embodiments, the processor 82 may use the vehicle operation information to determine whether there is an indication that the user 26 is impaired (from block 144). For example, the vehicle operation information may include indications of erratic driving behavior, such as swerving of the vehicle 12, abrupt changes in direction of the vehicle 12, lane changes without proper signaling, approaching other vehicles within a threshold distance, abrupt changes in speed of the vehicle 12, and so on.

The processor 82 then determines (block 148) whether there is an indication that the user 26 is driving the vehicle 12. Specifically, the processor 82 may determine whether the vehicle operation information received in block 146 indicates that the vehicle 12 is in operation (e.g., in active operation) and/or that the user 26 is driving the vehicle 12. That is, the processor 82 may determine whether vehicle operation information received from an engine sensor indicates that the engine 16 is running, whether vehicle operation information received from a battery sensor indicates that the battery 18 is being drained, whether vehicle operation information received from an alternator sensor indicates that the alternator 20 is attempting to start the vehicle 12, whether vehicle operation information received from a wheel sensor indicates that the wheel 22 is rotating, or whether vehicle operation information received from a rear facing camera 23 indicates that the vehicle 12 is moving. As another example, the processor 82 may determine whether vehicle operation information received from the orientation sensor 124 or a location device of the mobile electronic device 24 indicates that the vehicle 12 is moving or in operation. In additional or alternative embodiments, the processor 82 may determine whether vehicle operation information received by the location application 102 of the mobile electronic device 24 indicates that the vehicle 12 is moving or in operation.

In some embodiments, the processor 82 may determine that the user 26 is driving the vehicle 12, as opposed to the user 26 merely being a passenger in the vehicle 12. For example, the processor 82 may request or prompt the user 26 (e.g., via an audio output device 112 such as a speaker) to answer whether he or she is driving the vehicle 12. In additional or alternative embodiments, the processor 82 may automatically determine whether the user 26 is driving the vehicle. For example, the processor 82 may communicate with a vehicle sensor of the vehicle 12 (e.g., the occupancy sensor 34 disposed in the driver seat 36 of the vehicle 12 or the pulse detection sensor 30 disposed in the steering wheel 32 of the vehicle 12) to determine a distance between the mobile electronic device 24 and a part of the vehicle 12 associated with driving, such as the driver seat 36 or the steering wheel 32. If the distance is within a threshold distance, the processor 82 may determine that the user 26 is driving the vehicle 12. In additional or alternative circumstances, the processor 82 may determine there is an indication that the user 26 is driving the vehicle 12 based on analyzing movements of the mobile electronic device 24 and determining whether such movements correspond to user movements typically associated with a driver. For example, the orientation sensor 124 (e.g., a gyroscope and/or an accelerometer) of the mobile electronic device 24 may indicate that the user 26 is entering the driver side of the vehicle 12 based on the direction of movement experienced by the orientation sensor 124 (e.g., corresponding to twisting motions of the user 26 when entering the driver side of the vehicle 12). As another example, one or more audio sensors 122 (e.g., microphones) of the mobile electronic device 24 may indicate that the user 26 is sitting in the driver seat of the vehicle 12 based on determining the direction(s) of radio sounds or road noise. It should be understood that any suitable technique, including those discussed above, may be used to provide an indication that the user 26 is driving the vehicle 12. Moreover, any combination of techniques may be used to provide an indication that the user 26 is driving the vehicle 12, and any system of accumulating and weighting the results or values resulting from the techniques may be used to provide an indication that the user 26 is driving the vehicle 12.

If the processor 82 determines that there is not an indication that the user 26 is driving the vehicle 12, then the method 140 repeats. Otherwise, the processor 82 determines that the user 26 is driving the vehicle 12, and performs (block 150) an action based on the user being impaired and driving. The action may include alerting the user 26 via a tactile response, audio response, and/or visual response. For example, the action may use the alarm application 110 (e.g., via the audio output device 112 of the mobile electronic device 24) to alert the user 26. As another example, the processor 82 may use the insurance company application 98 to alert a representative of the insurance company, who may take action to prevent the user 26 from operating the vehicle 12, such as by contacting the user 26. Similarly, the processor 82 may use the social media application 94 to communicate with a member of a virtual community or network that is familiar to the user 26, who may then contact the user 26.

The action may also include offering alternatives to operating the vehicle 12 while impaired. For example, the processor 82 may use the insurance company application 98 to alert a representative of the insurance company, who may attempt to arrange alternative means of transport (e.g., a taxi) for the user 26. As another example, the processor 82 may use the social media application 94 to communicate with a member of a virtual community or network that is familiar to the user 26 for the member to pick up the user 26. As yet another example, the processor 82 may use the transportation application 96 to request transportation from a transportation company for the user 26. In one embodiments, the processor 82 may reroute a mapping software application program (e.g., provide directions) to direct the user 26 and/or the vehicle 12 to a location suitable for the user 26 to stop the vehicle 12 (e.g., a rest stop, a restaurant, a public park, and so on).

In some embodiments, the action may include incentivizing the user 26 to not operate the vehicle 12 while impaired. For example, the processor 82 may use the insurance company application 98 to offer discounts associated with auto insurance provided by the insurance company, offer discounts on affiliated products or services, or use gaming elements to encourage not driving while impaired. The gaming elements may include any suitable gamification techniques that may encourage the user 26 not driving while impaired, such as rewarding the user 26 with points, achievement badges or levels, filling a progress bar, and/or providing the user 26 with virtual currency. Similarly, the action may include penalizing the user 26 for operating the vehicle 12 while impaired. For example, the processor 82 may use the insurance company application 98 to increase payments associated with auto insurance provided by the insurance company or use gaming elements to penalize driving while impaired. Such gaming elements may include any suitable gamification techniques that may discourage the user 26 from driving while impaired, such as decreasing user points, taking away achievement badges or levels, decreasing a progress bar, and/or taking away virtual currency.

The action may also include warning nearby drivers (e.g., by activating hazard lights of the vehicle via an interface between the vehicle and the mobile device) or autonomous vehicles. For example, the processor 82 may warn nearby drivers or autonomous vehicles that the user 26 may be impaired via the communication interface 114. In some embodiments, the processor 82 may receive proximity information from proximity sensor(s) of the vehicle 12 to determine whether there are any nearby vehicles within a threshold distance (e.g., 0-50 feet or 2-25 feet) to the vehicle 12. In additional or alternative embodiments, the processor 82 may communicate with mobile devices of drivers of the nearby vehicles and/or communication devices of the nearby vehicles or autonomous vehicles using the communication interface 114 to determine whether there are any nearby vehicles within the threshold distance. The processor 82 may then send alerts to the mobile devices of drivers of the nearby vehicles and/or communication devices of the nearby vehicles or autonomous vehicles using the communication interface 114 to inform them that the user 26 may be impaired. The method 140 then repeats. In this manner, the method 140 may reduce impaired driving.

While the embodiments set forth in the present disclosure may be susceptible to various modifications and alternative forms, specific embodiments have been shown by way of example in the drawings and have been described in detail herein. However, it should be understood that the disclosure is not intended to be limited to the particular forms disclosed. The disclosure is to cover all modifications, equivalents, and alternatives falling within the spirit and scope of the disclosure as defined by the following appended claims.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

What is claimed is:

1. One or more tangible, non-transitory, machine-readable media, comprising machine-readable-medium instructions that, when executed by processing circuitry of a mobile electronic device, cause the processing circuitry to:
   determine that a driver is attempting to operate a vehicle based on vehicle operation data from one or more vehicle operation sensors of the vehicle;
   receive sensor data from a vehicle sensor of a part of the vehicle associated with driving, indicating a position of a user within the vehicle;
   determine a distance between the part of the vehicle and a position of a mobile electronic device based on the sensor data;
   determine that the user is the driver based on the distance between the part of the vehicle and the position of mobile electronic device being within a threshold distance;
   receive sleep pattern information indicative of a time frame associated with when the user associated is typically asleep;
   determine a risk factor based on the sleep pattern information;
   increase the risk factor in response to determining that a current time at which the user is attempting to operate the vehicle corresponds to the time frame associated with when the user is typically asleep; and
   perform an action to prevent the user from operating the vehicle in response to determining that the risk factor is above a threshold.

2. The one or more tangible, non-transitory, machine-readable media of claim 1, wherein the sensor data from the mobile electronic device is indicative of movement, and wherein the instructions cause the processing circuitry to determine that the user is the driver by:
   determining a direction of movement of the user entering the vehicle; and determining that the user is the driver based on the direction of movement corresponding to the user entering the driver side of the vehicle.

3. The one or more tangible, non-transitory, machine-readable media of claim 1, wherein the sensor data from the mobile electronic device comprises audio data, and wherein the instructions cause the processing circuitry to determine the user is the driver by: causing an audio device to output a voice prompt for the driver; receiving the sensor data comprising the audio data subsequent to outputting the voice prompt; and determining the user is the driver based on the audio data confirming that the user is driving the vehicle.

4. The one or more tangible, non-transitory, machine-readable media of claim 1, wherein the sensor data from the mobile electronic device is indicative of movement, and wherein the instructions cause the processing circuitry to determine the user is the driver by determining that the movement corresponds to that of the driver.

5. The one or more tangible, non-transitory, machine-readable media of claim 1, wherein the action comprises providing a travel recommendation to the user via the mobile electronic device of the user.

6. The one or more tangible, non-transitory, machine-readable media of claim 1, wherein the vehicle operation data comprises data indicating that a battery of the vehicle is being drained.

7. A method, comprising:
   receiving, via processing circuitry of a mobile electronic device, sleep pattern information that is indicative of a time frame associated with when a user is typically asleep;
   receiving, via the processing circuitry, vehicle operation data from one or more vehicle operation sensors of a vehicle associated with driving indicating the user is attempting to start the vehicle;
   determining, via the processing circuitry, a risk factor based on the sleep pattern information and the vehicle operation data;
   determining, via the processing circuitry, a current time at which the user is attempting to start the vehicle;
   receiving, via the processing circuitry, a first sensor data from the mobile electronic device of the user;
   receiving, via the processing circuitry, a second sensor data from a sensor associated with a part of the vehicle;
   determining, via the processing circuitry, a distance between the part of the vehicle and a position of the mobile electronic device based on the first sensor data and the second sensor data;
   determining, via the processing circuitry, that the user is a driver of the vehicle based on the distance between the part of the vehicle and the mobile electronic device being within a threshold distance;
   increasing, via the processing circuitry, the risk factor in response to determining that the current time at which the vehicle is being operated corresponds to the time frame associated with when the user is typically asleep; and
   performing, via the processing circuitry, an action to prevent the user from operating the vehicle in response to determining that the risk factor is above a threshold.

8. The method of claim 7, comprising: determining, via the processing circuitry, a direction of a source of noise relative to a position of the mobile electronic device; and determining, via the processing circuitry, that the user is the driver based on the direction of the source of noise relative to the position of the mobile electronic device indicating the user is in a driver seat within the vehicle.

9. The method of claim 7, comprising: determining, via the processing circuitry, a direction of movement of the user entering the vehicle based on the first sensor data; and determining, via the processing circuitry, that the user is the driver based on the direction of movement corresponding to the user entering a driver side of the vehicle.

10. The method of claim 7, wherein the action comprises modifying points of a gaming profile associated with the user in response to determining that the user is the driver.

11. The method of claim 7, wherein the action comprises contacting one or more contacts of the user based on information associated with one or more contacts stored in the mobile electronic device associated with the user.

12. The method of claim 7, wherein the sensor associated with the part of the vehicle comprises a steering wheel sensor.

13. A system comprising:
   a first sensor of a part of a vehicle configured to detect vehicle operation data of the vehicle; the first sensor of the vehicle being associated with driving; and
   a mobile electronic device communicatively coupled to the first sensor, wherein the mobile electronic devices comprises one or more processors and one or more memory devices, wherein the one or more memory devices store instructions that, when executed by the one or more processors, cause the one or more processors to:

receive sleep pattern information, wherein the sleep pattern information is indicative of a time frame associated with when a user is typically asleep;

receiving vehicle operation data, wherein the vehicle operation data indicates that the user is attempting to start the vehicle;

determine a risk factor based on the sleep pattern information and the vehicle operation data;

receive sensor data from a second sensor of the mobile electronic device;

determine a distance between the part of the vehicle and a position of a mobile electronic device based on sensor data acquired by the first sensor and the second sensor;

determine that the user is the driver based on the distance between the part of the vehicle and the position of mobile electronic device being within a threshold distance;

increase the risk factor in response to determining that a current time at which the vehicle is being operated corresponds to the time frame associated with when the user is typically asleep; and perform an action to prevent the user from operating the vehicle in response to determining that the risk factor exceeds a threshold.

14. The system of claim 13, wherein the sensor data comprises audio data, and wherein the instructions cause the one or more processors to determine the user is the driver based on the audio data.

15. The system of claim 13, wherein the sensor data comprises movement data, and wherein the instructions cause the one or more processors to determine the user is the driver based on the movement data.

16. The system of claim 13, wherein the sleep pattern information is stored in the one or more memory devices of the mobile electronic device of the user.

17. The system of claim 13, wherein the second sensor comprises a steering wheel sensor.

* * * * *